US008187165B2

(12) United States Patent
Park

(10) Patent No.: US 8,187,165 B2
(45) Date of Patent: May 29, 2012

(54) PORTABLE SPHINCTER TRAINING TOOL

(76) Inventor: Young Jin Park, Daejeon (KR)

( * ) Notice: Subject to any disclaimer, the term of this patent is extended or adjusted under 35 U.S.C. 154(b) by 988 days.

(21) Appl. No.: 12/093,864

(22) PCT Filed: Nov. 15, 2006

(86) PCT No.: PCT/KR2006/004804
§ 371 (c)(1),
(2), (4) Date: May 15, 2008

(87) PCT Pub. No.: WO2007/058466
PCT Pub. Date: May 24, 2007

(65) Prior Publication Data

US 2008/0300452 A1 Dec. 4, 2008

(30) Foreign Application Priority Data

Nov. 15, 2005 (KR) .................. 20-2005-00032309 U

(51) Int. Cl.
*A61F 5/00* (2006.01)
(52) U.S. Cl. ......................................................... 600/41
(58) Field of Classification Search ............... 600/38–41
See application file for complete search history.

(56) References Cited

U.S. PATENT DOCUMENTS 7,802,577 B2 * 9/2010 Cvetanovic .................. 128/845
2003/0036464 A1 2/2003 Zavilevich
2005/0101452 A1 5/2005 Dana, III
2007/0156014 A1 * 7/2007 Zafirakis ........................ 600/41
2009/0318754 A1 * 12/2009 Ettmer ........................... 600/38
2010/0016656 A1 * 1/2010 Rudi .............................. 600/39

FOREIGN PATENT DOCUMENTS

JP 06-039056 2/1994
KR 20-0399545 10/2005

* cited by examiner

*Primary Examiner* — John Lacyk
(74) *Attorney, Agent, or Firm* — Park & Associates IP Law, P.C.

(57) ABSTRACT

Disclosed is a portable sphincter training tool in that the general male can wear on his body and naturally exercise his sphincter at recess or in the course of daily life, whereby improving physically and spiritually in vitality and confidence. The portable sphincter training tool comprises a penis induction pipe for receiving a penis; an adhesive plate coupled to the penis induction pipe, adhered to an user's body during wear and having a vacuum pump for making the penis induction pipe vacuous; and a sphincter tension necklace coupled to one side of the adhesive plate and hanged on an user's neck in order to stably adhere the penis induction pipe to the adhesive plate and apply a tension to the sphincter according to a predetermined movement during adhesion; wherein an insertion portion of the penis induction pipe is bent inward in such a manner that the penis is stably received upward.

3 Claims, 1 Drawing Sheet

[Fig. 1]
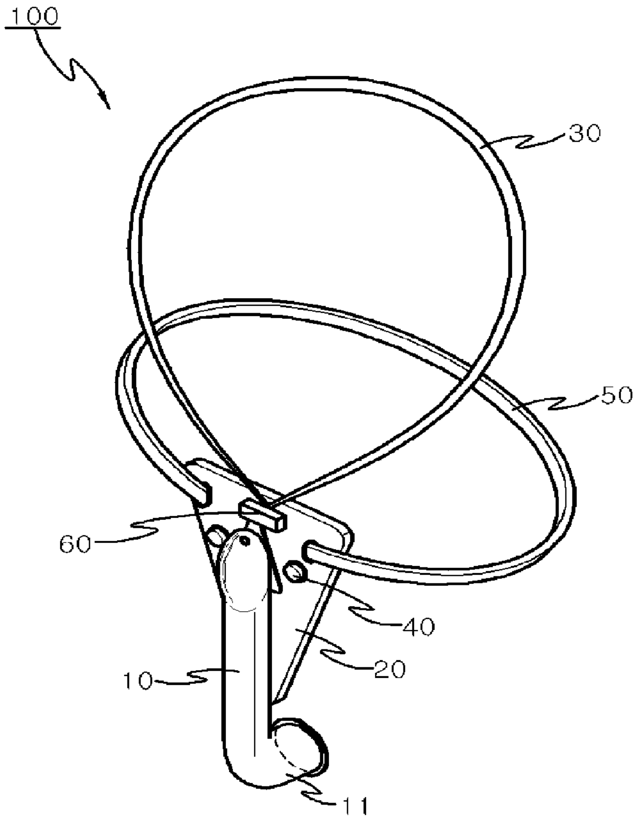
[Fig. 2]
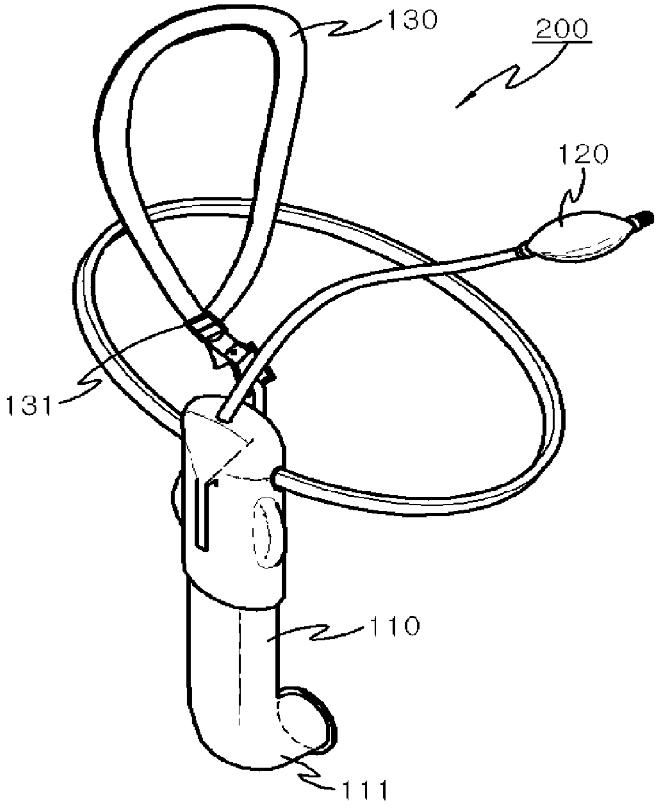

PORTABLE SPHINCTER TRAINING TOOL

TECHNICAL FIELD

The present invention relates to a portable sphincter training tool and more particularly, to a portable sphincter training tool, in that the general male can wear on his body and naturally exercise his sphincter at recess or in the course of daily life, whereby improving physically and spiritually in vitality and confidence.

BACKGROUND ART

Generally, a linear type vacuum inspirator is disclosed in that a penis of an user is sucked through only the linear type vacuum inspirator and a rubber ring for blocking out a bloodstream of the penis is inserted, thereby maintaining the erection of the penis only during sexual relations. The conventional vacuum inspirator serves to only block out the sucked bloodstream. However, it has no effect on the sphincter exercise. Also, since the vacuum inspirator cannot be worn on a body of the user, it cannot exercise the sphincter with his family or other persons at recess or in the course of daily life. Accordingly, because the user should confidentially exercise alone, it is impossible to steadily exercise his sphincter.

Also, since the conventional vacuum inspirator of men's penis is a straight linear type, the penis is protruded forwardly during the exercise, thereby it requires a confidential space capable of exercising along. Moreover, because it cannot be worn on a body of the user, there is a problem in that the vacuum suction thereof should be performed in a state of holding it in both hands.

DISCLOSURE OF INVENTION

Technical Problem

It is, therefore, an object of the present invention to provide a portable sphincter training tool for vacuum-inspiriting a men's penis, in that a waist belt and a sphincter tension necklace are provided so as to be worn on his body and a bent induction pipe is formed in a penis insertion portion of a vacuum induction pipe, so that the penis is not protruded forwardly and it can be stably worn, thereby naturally exercising his sphincter at recess or in the course of daily life.

Another object of the present invention to provide a portable sphincter training tool, in that it can be operated with one hand and massage a sphincter by means of a vacuum pump and a vibration motor formed at an adhesive plate during wear.

Technical Solution

To achieve the above objects of the present invention, there is provided a portable sphincter training tool comprising: a penis induction pipe for receiving a penis; an adhesive plate coupled to the penis induction pipe, adhered to an user's body during wear and having a vacuum pump for making the penis induction pipe vacuous; and a sphincter tension necklace coupled to one side of the adhesive plate and hanged on an user's neck in order to stably adhere the penis induction pipe to the adhesive plate and apply a tension to the sphincter according to a predetermined movement during adhesion; wherein an insertion portion of the penis induction pipe is bent inward in such a manner that the penis is stably received upward.

Here, a vibration motor is further formed at the adhesive plate in order to massage it by means of the vibration thereof.

Also, to achieve the above objects of the present invention, there is provided a penis induction pipe for receiving a penis and having an insertion portion bent inward in order to stably receive the penis upward; a vacuum pump for adjusting an amount of an air of the penis induction pipe coupled to the penis induction pipe in order to stably fix the penis; and a sphincter tension necklace coupled to one side of the penis induction pipe and hanged on an user's neck in order to stably adhere the penis induction pipe and apply a tension to the sphincter according to a predetermined movement during adhesion.

ADVANTAGEOUS EFFECTS

As described above, according to the portable sphincter training tool, the waist belt and sphincter tension necklace capable of easily wearing on his body, the vacuum pump capable of operating with one hand, and the vibration motor for massage are provided, the general male can easily wear on his body and naturally exercise his sphincter at recess, whereby improving physically and spiritually in vitality and confidence, without taking medicine such as a Viagra and so on or undergoing any surgical operation.

BRIEF DESCRIPTION OF THE DRAWINGS

The above as well as the other objects, features and advantages of the present invention will be more apparent from the following detailed description taken in conjunction with the accompanying drawings, in which:

FIG. 1 is a perspective view illustrating a portable sphincter training tool according to one embodiment of the present invention; and FIG. 2 is a perspective view illustrating a portable sphincter training tool according to another embodiment of the present invention.

BEST MODE FOR CARRYING OUT THE INVENTION

A preferred embodiment of the invention will be described in detail below.

FIG. 1 is a perspective view illustrating a portable sphincter training tool according to one embodiment of the present invention.

As shown in FIG. 1, the portable sphincter training tool 100 according to one embodiment of the present invention comprises a penis induction pipe 10 for receiving a penis, an adhesive plate 20 coupled to the penis induction pipe 10, adhered to an user's body during wear and having a vacuum pump 40 for making the penis induction pipe 10 vacuous, and a sphincter tension necklace 30 coupled to one side of the adhesive plate 20 and hanged on an user's neck in order to stably adhere the penis induction pipe 10 to the adhesive plate 20 and apply a tension to the sphincter according to a predetermined movement during adhesion.

The penis induction pipe 10 servers to receive the user's penis. The portable sphincter training tool 100 according to the present invention is best characterized in that the penis is received upward and adhered to the underbelly of the user by means of the penis induction pipe 10.

Accordingly, in order to remove the inconvenience of the user, an insertion portion 11 of the penis induction pipe 10 is bent inward at a predetermined angle (90 degrees in the drawing).

Also, the adhesive plate 20 is coupled to the penis induction pipe 10 and adhered to the underbelly of the user. The vacuum pump 40 of the adhesive plate makes the penis induction pipe 10 vacuous.

Accordingly, the penis received in the penis induction pipe 10 is fixed and the sphincter thereof is under impetus from the following sphincter tension necklace 30.

The vacuum pipe 40 is communicated with the penis induction pipe 10 via a pre-determined space formed in the inside of the adhesive plate 20 and automatically pumped in the type of an electric motion. However, the vacuum pipe 40 can be directly communicated with one side of the penis induction pipe 10 in order to manually pump it.

In the meantime, the sphincter tension necklace 30 is coupled to one side of the adhesive plate 20 and hanged on the user's neck in order to stably adhere the penis induction pipe 10 to the adhesive plate 20. As described above, the sphincter tension necklace 30 can apply the tension to the sphincter according to the waist or head movement during adhesion.

Also, the sphincter tension necklace 30 further includes a length adjuster for appropriately adjusting the length thereof according to the body condition of the user. Moreover, the portable sphincter training tool 100 according to the present invention can further include a waist belt 50 for stably fixing it.

As shown in FIG. 1, the waist belt 50 is coupled to the adhesive plate 20 in order to wrap the user's waist.

Also, a vibration motor 60 is formed at the adhesive plate 20 in order to massage it by means of the vibration thereof. Preferably, the vibration motor 60 can control the operating condition thereof according to the choice of user.

The operation of the portable sphincter training tool will be described in detail below.

Firstly, the massage oil is applied on the penis of the user and the penis is inserted in the insertion portion 11 of the penis induction pipe 10. Then, the vacuum pipe 40 is operated, so that the penis of the user is sucked in the penis induction pipe 10 along the bent insertion portion 11 by means of the suction power thereof.

Continuously, where the penis of the user is sucked in the penis induction pipe 10, the vibration motor 60 is operated and the waist of the user is stretched. Then, the waist belt 50 and the sphincter tension necklace 30 are drawn and the adhesive plate 20 connected to the vibration motor 60 is adhered to the underbelly of the user below the lower abdomen.

Accordingly, the sphincter connected to the sucked penis is naturally drawn and massaged by means of the vibration motor 60.

Here, where the sphincter is contracted, the stronger power is applied to the sphincter in comparison with the evacuation. Accordingly, in a case that the contracted training is periodically performed, the sphincter is well developed.

FIG. 2 is a perspective view illustrating a portable sphincter training tool according to another embodiment of the present invention.

As shown in FIG. 2, the portable sphincter training tool 200 according to another embodiment of the present invention comprises a penis induction pipe 110 for receiving a penis and having an insertion portion 111 bent inward in order to stably receive the penis upward, a vacuum pump 120 for adjusting an amount of an air of the penis induction pipe 110 coupled to the penis induction pipe 110 in order to stably fix the penis, and a sphincter tension necklace 130 coupled to one side of the penis induction pipe 110 and hanged on an user's neck in order to stably adhere the penis induction pipe 110 and apply a tension to the sphincter according to a predetermined movement during adhesion.

Since the portable sphincter training tool 200 according to another embodiment of the present invention has a simple construction in comparison with one embodiment of the present invention, the carrying and usage thereof is very easy.

The penis induction pipe 110 is inserted and fixed into the clothes or underwear of the user without being fixed to the adhesive plate 20 according to one embodiment of the present invention.

The vacuum pipe 120 is communicated with one side of the penis induction pipe 110 and the air of the penis induction pipe 110 is emitted, so that it makes the penis induction pipe 110 vacuous.

Also, the sphincter tension necklace 130 further includes a length adjuster for appropriately adjusting the length thereof coupled to one side of the penis induction pipe 110.

INDUSTRIAL APPLICABILITY

The present invention relates to a portable sphincter training tool and more particularly, to a portable sphincter training tool, in that the general male can wear on his body and naturally exercise his sphincter at recess or in the course of daily life, whereby improving physically and spiritually in vitality and confidence.

While this invention has been described in connection with what are presently considered to be the most practical and preferred embodiments, it is to be understood that the invention is not limited to the disclosed embodiments and the drawings, but, on the contrary, it is intended to cover various modifications and variations within the spirit and scope of the appended claims.

The invention claimed is:

1. A portable sphincter training tool comprising:

a penis induction pipe adapted to receive a penis;

an attachment plate coupled to the penis induction pipe, contacting a user's body during wear and having a vacuum pump for making the penis induction pipe vacuous; and a sphincter tension necklace coupled to one side of the attachment plate and configured to hang on the user's neck in order to hold the penis induction pipe to the attachment plate and apply a tension to the sphincter according to a predetermined movement during wearing for sphincter training;

wherein an insertion portion of the penis induction pipe is bent inward in such a manner that the penis is stably received upward.

2. A portable sphincter training tool as claimed in claim 1, wherein a vibration motor is attached to the attachment plate in order to massage the sphincter by means of the vibration thereof.

3. A portable sphincter training tool comprising:

a penis induction pipe adapted to receive a penis and having an insertion portion bent inward in order to stably receive the penis upward;

a vacuum pump for adjusting an amount of an air of the penis induction pipe, the vacuum pump coupled to the penis induction pipe to stably fix the penis;

and a sphincter tension necklace coupled to one side of the penis induction pipe and configured to hang on an user's neck in order to stably hold the penis induction pipe and apply a tension to the sphincter according to a predetermined movement during wearing for sphincter training.

* * * * *